United States Patent [19]
Tower

[11] Patent Number: 6,022,370
[45] Date of Patent: Feb. 8, 2000

[54] EXPANDABLE STENT

[75] Inventor: Allen J. Tower, North Lawrence, N.Y.

[73] Assignee: Numed, Inc., Nicholville, N.Y.

[21] Appl. No.: 08/937,396

[22] Filed: Sep. 25, 1997

Related U.S. Application Data

[60] Provisional application No. 60/027,345, Oct. 1, 1996.

[51] Int. Cl.[7] ................................................ A61M 29/00
[52] U.S. Cl. .............................................. 606/194; 606/195
[58] Field of Search .................................... 606/194, 191, 606/192, 195; 623/1

[56] References Cited

U.S. PATENT DOCUMENTS

| | | |
|---|---|---|
| 4,733,665 | 3/1988 | Palmaz . |
| 4,856,516 | 8/1989 | Hillstead . |
| 4,886,062 | 12/1989 | Wiktor . |
| 5,217,483 | 6/1993 | Tower . |
| 5,554,181 | 9/1996 | Das . |
| 5,630,840 | 5/1997 | Mayer . |
| 5,632,771 | 5/1997 | Boatman et al. . |
| 5,733,326 | 3/1998 | Tomonto ..................................... 623/1 |

*Primary Examiner*—Michael Buiz
*Assistant Examiner*—Vy Q. Bui
*Attorney, Agent, or Firm*—Wall Marjama Bilinski & Burr

[57] ABSTRACT

A radially expandable stent which is formed from a fine wire bent into a serpentine flat ribbon which is wound around a mandrel into a cylindrical sleeve for mounting on a balloon catheter for transluminal insertion in a vessel. The wire forming the stent comprises an alloy selected from the group consisting of Pt—Ir or Au—Ni, and where the alloy exhibits a tensile strength of about 155,000 to 175,000 PSI.

3 Claims, 2 Drawing Sheets

EXPANDABLE STENT

CROSS REFERENCE TO RELATED APPLICATION

Reference is made to and priority claimed from U.S. Provisional Application Ser. No. 60/027,345 filed Oct. 1, 1996, entitled Expandable Stent.

FIELD OF THE INVENTION

This invention relates to intravascular implants for maintaining vascular patency in human blood vessels. More particularly, this invention relates to a radially expandable stent made from a fine wire formed into a serpentine ribbon wound into a cylindrical shape for introduction into a body vessel for balloon expansion therein in a radial fashion to support the wall of the vessel when in the expanded configuration. This invention is particularly useful in transluminar implantation of a stent for use in the coronary angioplasty to prevent restenosis.

BACKGROUND OF THE INVENTION

The basic concept of stents has been known for a number of years. Various types of stents have been proposed and patented, including self-expanding spring types, compressed spring types, mechanically actuated expandable devices, heat actuated expandable devices, and the like. More recently, expandable sleeves have been proposed such as shown in U.S. Pat. No. 4,733,665 to Palmaz, issued Mar. 29, 1988. In this and other patents, Dr. Palmaz suggested a series of metal sleeves which could be expanded by a balloon catheter through the elastic limit of the metal so as to permanently deform them into contact and support of the interior surface of the blood vessel in question. Subsequently, patents to Hillstead, U.S. Pat. No. 4,856,516 issued Aug. 16, 1989 and U.S. Pat. No. 4,886,062 issued Dec. 12, 1989 to Wiktor, have shown stents formed of a zigzag wire wound around a mandrel in a somewhat cylindrical fashion which can then be mounted on a collapsed catheter balloon and expanded after introduction into the vessel by expanding the balloon catheter. These prior art devices have been satisfactory for certain installations, but have been limited in the amount of support that can be provided to the interior of the blood vessel wall and in some cases, to the ratio of expansion possible, and in other cases in the size of the profile presented for the transluminal insertion.

OBJECTS AND SUMMARY OF THE INVENTION

Accordingly, it is an object of the present invention to provide a stent that overcomes the limitations of the prior art.

It is a further object of the present invention to provide a fine wire stent that is economical to produce and yet exhibits the mechanical strength and elasticity to be able to maintain the desired shape and size in the expanded state after installation.

These and other objects of the present invention are accomplished in one embodiment by providing a stent formed from a fine wire bent into a flat serpentine ribbon and wound around a cylindrical mandrel to form a cylindrical sleeve for application to a collapsed balloon catheter for transluminal insertion in a blood vessel and later expansion by inflation of the balloon catheter at the desired site. In the present invention, the improvement comprises making the stent from a wire which comprises an alloy selected from the group consisting of Pt—Ir or Au—Ni, and where the alloy exhibits a tensile strength of about 155,000 to 175,000 PSI. In one embodiment of the present invention, the alloy comprises about 90 wt % Pt and 10 wt % Ir. It has been found that alloys of this type provide the combination of strength and resilience to be readily expandable and to maintain their size and shape in the expanded state after installation. In a further embodiment, the welds are eliminated and the free end of the wire forming the stent is looped or wrapped around the helix at a plurality of selected locations to provide for greater dimensional stability.

BRIEF DESCRIPTION OF THE DRAWINGS

These and other and further objects of the present invention with additional features and advantages accruing therefrom will be apparent from the following description shown in the accompanying drawings wherein.

DETAILED DESCRIPTION OF THE INVENTION

Figure 1:
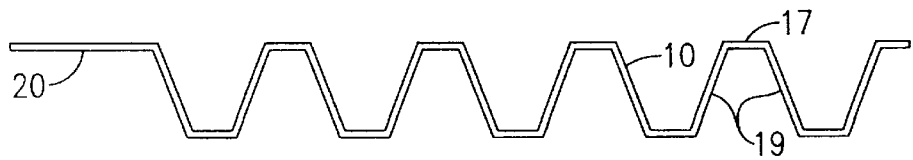
FIG. 1 is an enlarged scale plan view of the first step of the formation of a fine wire into the ribbon of the present invention.

Referring now to FIG. 1, a stent in accordance with the present invention and as illustrated by the prior art in U.S. Pat. No. 5,217,483 which is formed by first taking a fine wire 10 having a diameter of approximately 0.004 inch, preferably made from platinum and forming it into a generally sinusoidal form, as shown in FIG. 1 in which approximately ten cycles or segments per inch are formed in the wire. These waves can be formed in any convenient manner, for instance as by bending about a rack gear by running a corresponding spur gear over a wire laid along the rack.

Figure 2:
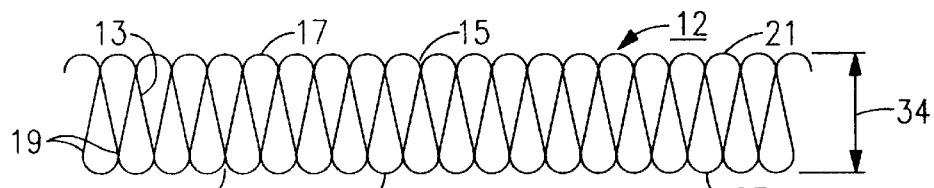
FIG. 2 is a view similar to FIG. 1 of the serpentine wire ribbon formed from the wire configuration of FIG. 1.

As may be seen in FIG. 2, the next step is to take the wire of FIG. 1 and to further bend the sinusoids into a flat band containing alternately inverted teardrop shaped elements or loops 13. Each element shares a common side with its neighbor and includes a base 17 and a pair of arcuate shaped legs 19—19 that come together in touching contact at an apex 15. The apex of a loop will lie along one side edge of the band, such as edge 21 while the base of the loop lies upon the opposite side edge 23 of the band. In this configuration, approximately forty loops 13 per inch of ribbon are present and the height or "amplitude" 34 of the loops is approximately 1/16 inch. This is accomplished by mechanically bending the partially formed loops of FIG. 1 up against each other into the shape shown in FIG. 2.

The fine wire 10 used to form the basic flat ribbon 12 is a soft platinum wire that has been fully annealed to remove as much spring memory as possible. The straight wire before bending, being in the fully annealed condition, will retain whatever shape it is formed into.

After the flat narrow serpentine ribbon 12 is formed, as shown in FIG. 2, the ribbon 12 is wrapped about a mandrel 14 having a diameter of 0.060 inch in a spiral or helix fashion with the edges of each helix wrap 16 of the ribbon 12 basically touching the adjacent ribbon helix edges to form a wire sleeve 18. The number of circumferential sections 16 on the mandrel will determine the length of the sleeve 18, and a typical stent of this type may have a length of approximately one-and-one-half inches.

Figure 3:
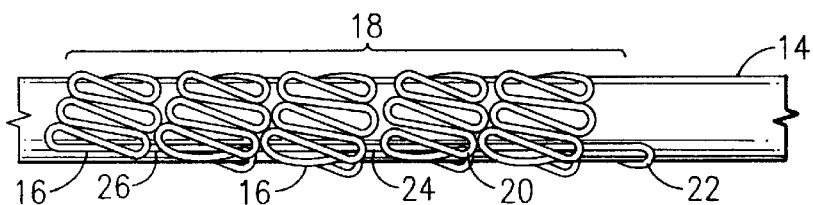
FIG. 3 is a view of the wire ribbon of FIG. 2 wound about a mandrel to form a helix; with the wire pigtail of the ribbon of FIG. 2 welded to the helix.

According to the present invention, as the serpentine ribbon 12 of FIG. 2 is wound on the mandrel 14 of FIG. 3, the free end 20 of the wire of FIG. 1 is inserted through the helix, as may be seen in FIG. 3. In actual practice, the ribbon 12 is wound about the mandrel 14 over the top of the free end 20 of the wire 10. After the helix is formed to the desired length, the free end 20 extending through the helix is trimmed, and welded smoothly to the final turn or end circumferential section of the helix 16 so as not to present any increased profile and so as not to puncture or pierce the balloon catheter or the blood vessel into which it is being inserted. The end turn of the helix is welded at 22 and intermediate welds such as 24 are formed to stabilize the length of the helix. The first turn of the helix at the other end may also be welded to the free end at 26 so that the overall length of the stent can be constrained and maintained in the desired configuration.

Figure 4:
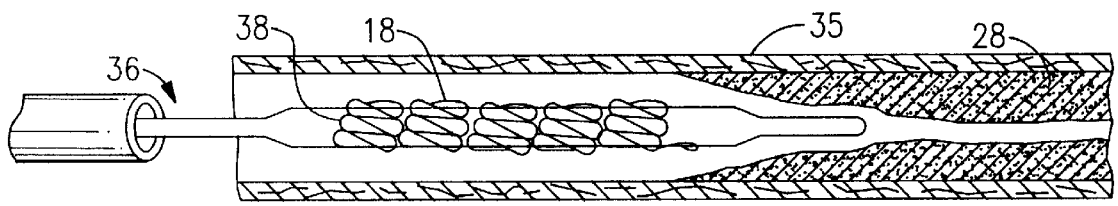
FIG. 4 is a view similar to FIG. 3 showing the stent mounted about a collapsed balloon catheter inserted in a blood vessel.

The serpentine ribbon sleeve 18 is next placed about a collapsed balloon catheter as shown in FIG. 4. In this configuration, the sleeve 18 generally has a diameter in the neighborhood of 1.5 mm for insertion into the blood vessels adjacent the heart.

Figure 5:
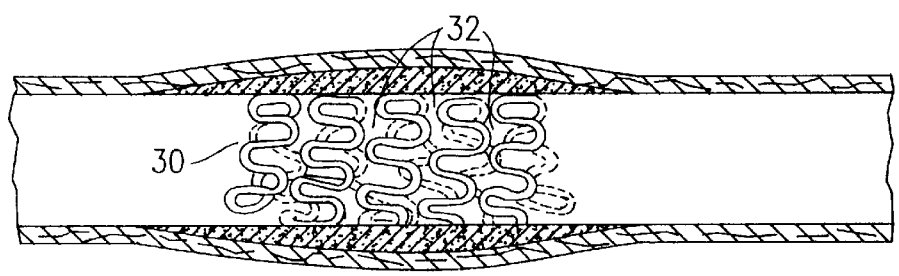
FIG. 5 is a view similar to FIG. 4 on a reduced scale showing the expanded stent in position in a blood vessel for holding the blood vessel in the open configuration.

In use, the stent is mounted on a balloon catheter as shown in FIG. 4 and is inserted into the appropriate blood vessel 35. The stent is guided to the desired location where there is occluding plaque 28 or a weak vessel wall or other imperfection requiring placement of a stent. Once the stent is properly located and verified by fluoroscopic or other means, the balloon catheter 36 is inflated to radially expand the serpentine wire sleeve 18. As the balloon 38 expands, it expands the tight closed apex of each loop of the serpentine ribbon 12 from "touching contact" shown in FIGS. 2–4 to a spaced apart condition as shown in FIG. 5. For instance, in a particular embodiment where the diameter of the stent on the collapsed balloon catheter was 1.5 mm, the stent has been expanded to 4 mm to 5 mm within the blood vessel. The space 30 between adjacent loops then increases to something approximately 0.0875 inch with the loop dimension being approximately 0.025 inch. Thus, what initially in FIG. 2 was a "wavelength" of 0.025 inch, now becomes a "wavelength" of 0.1125 inch. This is an increase of 4.5 times and is perhaps one of the more common expansion ratios found with stents of this type. With the present stent, expansion of up to 8 mm or six times has been found to be entirely satisfactory.

At the same time, the "amplitude" or width 34 of the ribbon 12 decreases some 20 percent to 25 percent due to the lengthening of the helix wrap due to the increased circumference of the expanded sleeve. Thus, as the helix 16 is lengthened by stretching the helix about the increased circumference of the expanded stent, the adjacent loops 13 are separated by spaces 30 at the same time the amplitude 34 of the individual helixes decrease. Also, the overall length of the sleeve 18 tends to decrease even to the point of causing the free end or pigtail 20 to bend between the welds 22, 24 and 26. The pigtail 20 prevents extension of the overall length of the sleeve 18, but allows it to contract as the diameter increases. The length tends to decrease because the middle of the balloon, and hence the middle of the stent, expands the most, pulling the ends toward the center.

It will be seen that this action maintains good interior surface support of the blood vessel by maintaining the close spacing of the wire loops and helixes forming the sleeve.

The expanded condition of the stent is shown in FIG. 5 with the balloon catheter having been removed and the back portion 32 of the sleeve 18 shown in dotted lines for clarity of presentation. Even in this expanded configuration, however, it will be seen that there are ample turns of wire spaced closely enough to fully support the inner surface of the blood vessel so as to prevent collapse of the plaque occluded vessel. With this "finer mesh" serpentine configuration, smaller diameter wire can be used without losing the necessary support for the interior surface of the blood vessel, and thus the stent presents a lower profile during introduction which increases the utility of the stent for smaller blood vessel usage. This "finer mesh" also results in a more flexible sleeve which, together with the smooth uniform surface of the tightly wound serpentine wire ribbon of FIGS. 2 and 3, improves the ease of transluminal insertion and facilitates proper implantation and location of the stent. Since the wire pigtail has no sharp ends and the free end is welded to the loop of the helix, there are no sharp edges or points to tear or catch on the catheter balloon or the interior surface of the blood vessel, and thus the stent of the present invention can be more readily manipulated to the desired location.

In prior art devices where the necessary surface support had to be achieved by heavier wire or a denser sleeve, it became difficult to flex the sleeve so as to transit the convoluted blood vessels. When a looser wire configuration was employed, the stability of the stent was decreased and the ultimate efficacy of the implanted stent compromised.

Since in one embodiment, the stent of the present invention is welded to the longitudinal wire at several locations, the longitudinal stability of the stent is greatly increased over the prior art devices without creating a stiff and inflexible stent that cannot be manipulated around curves and corners of the vessel into which it is to be introduced.

In some prior art applications, sleeves of platinum were objectionable because of its inherent high elastic limit such that it required extreme pressures to expand and to hold it in the expanded configuration without contraction sometimes causing insufficient support of the wall surfaces. With the serpentine construction of the present wire form, the elastic limit of in the annealed platinum wire can easily be overcome and the device can be fully expanded radially to support the blood vessel with very little pressure required from the balloon catheter. Thus, applicant is able to provide a stent which is more radiopaque than, for instance, stainless steel, without encountering the usual modulus of elasticity problems with platinum. This allows good visibility during implantation and speeds the procedure of positioning the stent in the proper location within the vessel.

In the present invention, the stent of the prior art described above in FIGS. 1–5 is made from a wire which comprises an alloy selected from the group consisting of Pt—Ir or Au—Ni, and where the alloy exhibits a tensile strength of about 155,000 to 175,000 PSI. In one embodiment of the present invention, the alloy comprises about 90 wt % Pt and 10 wt % Ir. It has been found that alloys of this type are an improvement over the prior art materials, and provide the combination of strength and resilience to be readily expandable, and to maintain their size and shape in the expanded state after installation.

Figure 6:
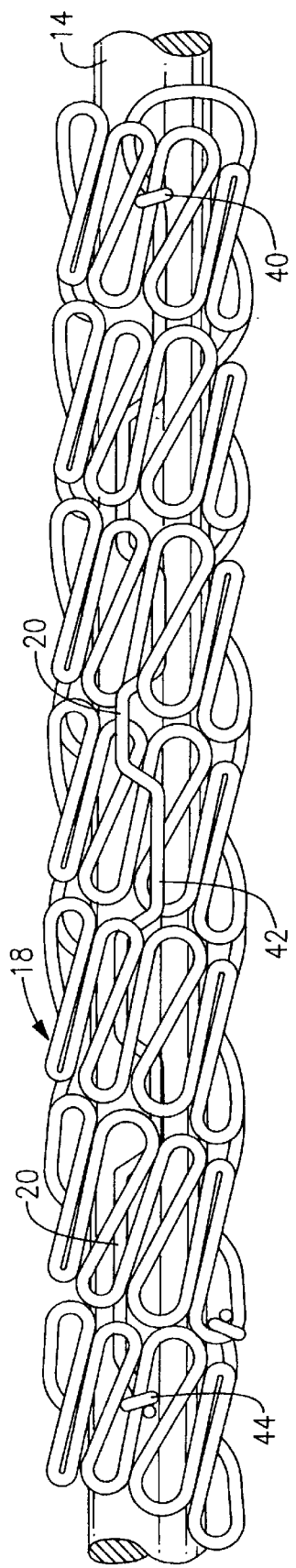
FIG. 6 is an enlarged view of the stent of the present invention wound about the mandrel similar to FIG. 3 except for the weld construction.

In a further improvement and preferred embodiment of the present invention as shown in FIG. 6, the welds 22, 24 and 26 as shown in FIG. 3, are eliminated and free end 20 is looped or wrapped (tied) around the helix at locations 40, 42 and 44. Wire 20 may overlap a given coil and move back under the next coil as shown at location 42. The tip of free end 20 is bent inwardly to avoid any surface profile and to avoid puncture or piercing the balloon catheter or blood vessel into which it is being inserted. It has been found that the loop and wrap configuration provides a greater dimensional stability to the expanded stent which overcomes the tendency of the prior art stents to prolapse with time.

Thus with the construction and configuration shown herein, there is provided a stent having good flexibility, dimensional stability, minimal impurities, very smooth surface, low profile and immunity to fatigue and corrosion.

While this invention has been explained with reference to the structure disclosed herein, it is not confined to the details set forth and this application is intended to cover any modifications and changes as may come within the scope of the following claims.

We claim:

1. A radially expandable stent for intravascular implantation that includes a plurality of helically aligned circumferential sections including two end sections and a plurality of intermediate sections that define a cylinder having a longitudinal axis, said cylinder formed of a continuous wire with said circumferential sections being spaced along said axis in abutting contact, each of said circumferential sections having expandable segments that impart radial expandability to said sections whereby said sections have an unexpanded insertion circumference and an expanded implantation circumference that is greater than said insertion circumference, said expandable segments being in their unexpanded mode, teardrop shaped elements that are alternately inverted about said circumferential sections, each element containing a base and a pair of legs that come together with a common apex when the stent is in a unexpanded condition, said expandable segments being in their expanded mode, U-shaped elements that are alternately inverted about said circumferential sections, one of said end sections having a free end that is passed back along the circumferential sections and is looped or wrapped around the circumferential sections at a plurality of preselected locations to provide dimensional stability and to prevent axial expansion of the stent during radial expansion.

2. The stent of claim 1 in which the wire forming the stent comprises an alloy selected from the group consisting of Pt—Ir or Au—Ni, and where the alloy exhibits a tensile strength of about 155,000 to 175,000 PSI.

3. The stent of claim 2 in which the alloy comprises about 90 wt % Pt and 10 wt % Ir.

* * * * *